(12) United States Patent
Badoz et al.

(10) Patent No.: US 7,785,174 B2
(45) Date of Patent: Aug. 31, 2010

(54) METHOD OF PRODUCING CUT BLADES FOR INSTRUMENTS USED IN ROOT CANAL TREATMENT

(75) Inventors: Jean-Marie Badoz, Doubs (FR); Franck Ponçot, Besançon (FR)

(73) Assignee: Micro Mega International Manufactures, Besançon (FR)

( * ) Notice: Subject to any disclaimer, the term of this patent is extended or adjusted under 35 U.S.C. 154(b) by 0 days.

(21) Appl. No.: 11/242,502

(22) Filed: Oct. 3, 2005

(65) Prior Publication Data
US 2006/0281047 A1 Dec. 14, 2006

(30) Foreign Application Priority Data
Jun. 14, 2005 (FR) .................................. 05 05987

(51) Int. Cl.
*B24B 7/30* (2006.01)
(52) U.S. Cl. ............................ 451/48; 433/102; 451/58
(58) Field of Classification Search ................. 433/102; 428/542.8; 29/896.1, 557; 451/48, 57–58
See application file for complete search history.

(56) References Cited

U.S. PATENT DOCUMENTS

| | | | |
|---|---|---|---|
| 4,443,193 A | 4/1984 | Roane |
| 4,604,884 A | 8/1986 | Matsutani |
| 4,634,378 A | 1/1987 | Leonard |
| 4,850,867 A | 7/1989 | Senia et al. |
| 4,934,934 A | 6/1990 | Arpaio, Jr. et al. |
| 5,464,362 A | 11/1995 | Heath et al. |
| 5,527,205 A | 6/1996 | Heath et al. |
| 5,628,674 A | 5/1997 | Heath et al. |
| 5,653,590 A | 8/1997 | Heath et al. |
| 5,655,950 A | 8/1997 | Heath et al. |
| 5,752,825 A | 5/1998 | Buchanan |
| 5,762,541 A | 6/1998 | Heath et al. |
| 5,855,479 A | 1/1999 | Wong et al. |
| 5,857,852 A | 1/1999 | Garman |
| 5,873,719 A | 2/1999 | Calas et al. |

(Continued)

FOREIGN PATENT DOCUMENTS

CH 670756 7/1989

(Continued)

OTHER PUBLICATIONS

Cavalli, Alain "Les Instruments Endodontiques dans la Préparation Canalaire" Thesis presented at Académie D'Aix-Marseilles, Mar. 29, 1982.

(Continued)

*Primary Examiner*—Cris L Rodriguez
*Assistant Examiner*—Hao D Mai
(74) *Attorney, Agent, or Firm*—Gary M. Cohen

(57) ABSTRACT

A blank for use in producing an endodontic instrument using a grinding technique includes a cylindrical portion, and a generally conical portion which is to be machined by the grinding technique to form the active part of the endodontic instrument. The generally conical portion of the blank approximates, and is slightly larger than the envelope of the final shape given to the active part of the endodontic instrument after machining. A method is also provided for producing an endodontic instrument having at least one helical cutting edge using the blank.

20 Claims, 3 Drawing Sheets

U.S. PATENT DOCUMENTS

| | | | |
|---|---|---|---|
| 5,882,198 A | 3/1999 | Taylor et al. | |
| 5,897,316 A | 4/1999 | Buchanan | |
| 5,902,106 A | 5/1999 | McSpadden | |
| 5,938,440 A | 8/1999 | McSpadden | |
| 5,941,760 A | 8/1999 | Heath et al. | |
| 5,975,899 A | 11/1999 | Badoz et al. | |
| 5,984,679 A | 11/1999 | Farzin-Nia et al. | |
| 6,074,209 A * | 6/2000 | Johnson | 433/102 |
| 6,206,695 B1 | 3/2001 | Wong et al. | |
| 6,299,445 B1 | 10/2001 | Garman | |
| 6,409,506 B1 * | 6/2002 | Graybill | 433/102 |
| 6,702,579 B1 * | 3/2004 | Hoppe et al. | 433/102 |
| 7,249,414 B2 | 7/2007 | Badoz | |
| 2004/0023186 A1 * | 2/2004 | McSpadden | 433/102 |
| 2004/0126734 A1 * | 7/2004 | Senia et al. | 433/102 |

FOREIGN PATENT DOCUMENTS

| | | |
|---|---|---|
| EP | 0719523 | 7/1996 |
| FR | 2747562 | 10/1997 |
| FR | 2755845 | 5/1998 |
| WO | WO9721392 | 6/1997 |
| WO | WO9740771 | 11/1997 |
| WO | WO9803126 | 1/1998 |
| WO | WO9803127 | 1/1998 |
| WO | WO9937235 | 7/1999 |
| WO | WO 9943469 | 9/1999 |
| WO | WO 0245612 | 6/2002 |

OTHER PUBLICATIONS

European Standard EN ISO 1797-1 "Dental Rotary Instruments—Shanks" (1995).

Henry, Sylvie Yguel, "Test d'Efficacité des Instruments Endodontiques Utilises en Traction Pure: Mise au Point d'un Protocole Expérimental Original", Thesis presented at Académie De-Nancy-Metz, Jul. 6, 1988.

Spohr, Marie-Christine, "Propriétés Biomécaniques des Instruments Endodontioues: Actualisation", Thesis presented at Académie De Nancy-Metz, Apr. 29, 1987.

Walia et al., "An Initial Investigation of the Bending and Torsional Properties of Nitinol Root Canal Files" Journal of Endodontics, vol. 14, No. 7, pp. 346-351 (Jul. 1988).

RMI Titanium, RMI Company, Niles, Ohio, 27 pages (1991).

Stoeckel, Dieter, et al., "Superelastic Ni-Ti Wire", Wire Journal International, pp. 45 to 50 (Mar. 1991).

* cited by examiner

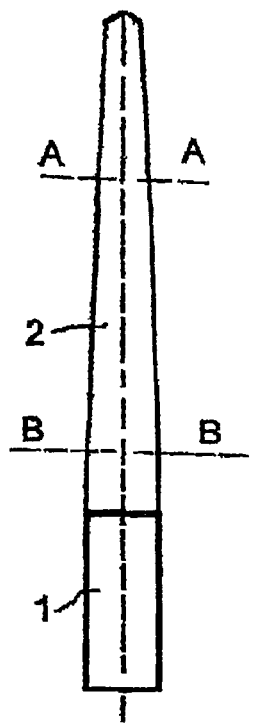
FIG. 1
FIG. 1A
FIG. 1B
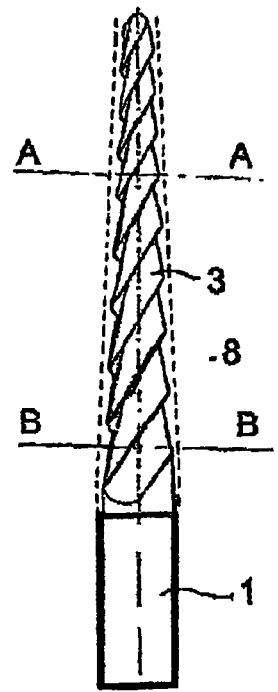
FIG. 2
FIG. 2A
FIG. 2B

METHOD OF PRODUCING CUT BLADES FOR INSTRUMENTS USED IN ROOT CANAL TREATMENT

BACKGROUND OF THE INVENTION

The present invention generally relates to the field of endodontic instruments, and more particularly, to a conical blank and to a method of producing cut blades for instruments used in root canal treatment.

Endodontic instruments of this type are mainly composed of a blade and a shaft. The blade is inserted into the dental cavity to be treated and requires a high degree of flexibility in order to follow the path of the root canal in the tooth. A high degree of mechanical strength is also required in order not to accidentally break the blade during working of the canal. The blade defines an active part having a generally conical shape.

Such blades were initially made of steel. As these blade were used, however, it became apparent that steel was not sufficiently flexible and strong to satisfy the demands placed on the blades, particularly considering the small diameter of such blades.

An article by Walia et al., published in the Journal of Endodontics in July of 1988 (Volume 14, No. 7, pages 346-351), described the production of endodontic instruments from a nickel/titanium alloy. In particular, K-type files were made from a wire of nickel/titanium with a diameter of 0.020 inches (i.e., about 0.508 mm), using a method which started directly from a blank cut in the wire.

Using the very strong nickel/titanium alloys satisfied the basic requirements for endodontic applications, but posed a problem concerning the speed of the machining operation. This, in turn, posed a problem relative to the cost of manufacturing cut blades using the traditional grinding techniques employing cylindrical blanks.

Endodontic instruments, for example, those known as Hedstroem files, have for many years been made by machining, in particular, by grinding. The process begins with a cylindrical blank, which is brought in front of a grinder. The grinder has a configuration such that machining of the blank produces a groove in the blank, i.e., a "cutting edge", and provides the instrument with a desired conicity by virtue of the combined advancement of the blank in front of the grinder, and of rotation of the blank about its axis. Such instruments are described, for example, in standard ISO 3630.

Methods for producing blades having one or more cutting edges are known, in particular, from U.S. Pat. No. 5,527,205, U.S. Pat. No. 5,628,674 and U.S. Pat. No. 5,655,950, which describe the use of cylindrical blanks formed of alloys of at least 40% titanium and about 50% nickel, and having a diameter of less than 0.07 inches. The blades obtained by the disclosed methods have at least one channel cut in a helical formation, in a single pass (i.e., displacement) in front of the grinder. The disclosed methods are said to obtain blades which are free from defects, and without deformation of the metal. U.S. Pat. No. 5,527,205 and U.S. Pat. No. 5,655,950 additionally specify that at least 25% of the diameter of the cylindrical blank is removed from the portions of the blade which are to perform the greatest amount of cutting.

Such processes for producing conical endodontic instruments from a cylindrical blank were known at the time the above-identified patents were filed. For example, such methods were disclosed by Sylvie Yguel Henry, in a thesis presented in Nancy, France on Jul. 6, 1988, and by Marie-Christine Spohr, in a thesis presented in Nancy, France on Apr. 29, 1987. Such production methods were also discussed by Alain Cavalli, in a thesis presented in Marseilles, France on Mar. 29, 1982.

Producing cut blades from a cylindrical blank, whether formed of steel or formed of a nickel/titanium alloy, entails considerable difficulty in obtaining the overall conical shape of the cut blade. This conicity can vary from one piece to another, and in all cases, portions of the cut blade will have a reduced cross-section, which then requires a substantial removal of material by abrasion.

For portions of the cut blade which have a greater diameter, closer to the diameter of the cylindrical blank, the cutting speed can be more rapid. This, however, results in a differential removal of material along the cut part, which in turn poses various technical problems resulting in a considerable length of time for the production of the machined piece. This then results in a high cost for the production of each endodontic instrument.

Consequently, it is the object of the present invention to improve the speed of production for cut blades usable in the endodontic field, and more particularly, to solve this principal difficulty in association with the production of instruments made of nickel/titanium.

SUMMARY OF THE INVENTION

The present invention generally relates to a blank for use in producing an endodontic instrument by grinding, and to a method for producing an endodontic instrument provided with at least one helical cutting edge, using such a blank. The blank has a cylindrical portion, and a generally conical portion which is to be machined to form the active part of the final endodontic instrument. The conical portion of the blank approximates, and is slightly larger than the envelope of the final shape given to the active part of the endodontic instrument after machining.

Use of the blank of the present invention makes it possible to avoid the lengthy machining of the excess material, i.e., the material situated above the envelope of the desired endodontic instrument, particularly at the thinner end portions of the instrument. Along these thinner, tapered end portions, over 60% of the material associated with prior cylindrical blanks can in some cases have to be removed during the grinding process. In accordance with the present invention, the amount of material to be removed by the grinding process is significantly reduced.

As a result, the principal advantage of a blank having a generally conical portion, and of a method for machining such a blank, in accordance with the present invention, is improvement of the speed of production of the endodontic instruments which are produced from such blanks. This is particularly so for the production of instruments made from materials which are strong and difficult to machine, of which a representative example is nickel/titanium alloys. Improvement of the speed of production logically translates into a reduction in the cost of manufacture of the instrument.

Other characteristics and advantages of the present invention will become clear from the description of non-limiting examples which follows, with reference to the following drawings.

BRIEF DESCRIPTION OF THE DRAWINGS

FIG. 1 is an elevational view of a conical blank of the present invention, before machining.

FIG. 1A is a cross-sectional view of the blank shown in FIG. 1, taken along the line A-A.

FIG. 1B is a cross-sectional view of the blank shown in FIG. 1, taken along the line B-B.

FIG. 2 is an elevational view of the conical blank shown in FIG. 1, after machining.

FIG. 2A is a cross-sectional view of the blank shown in FIG. 2, taken along the line A-A.

FIG. 2B is a cross-sectional view of the blank shown in FIG. 2, taken along the line B-B.

DETAILED DESCRIPTION OF THE INVENTION

Figures 3A, 3B:
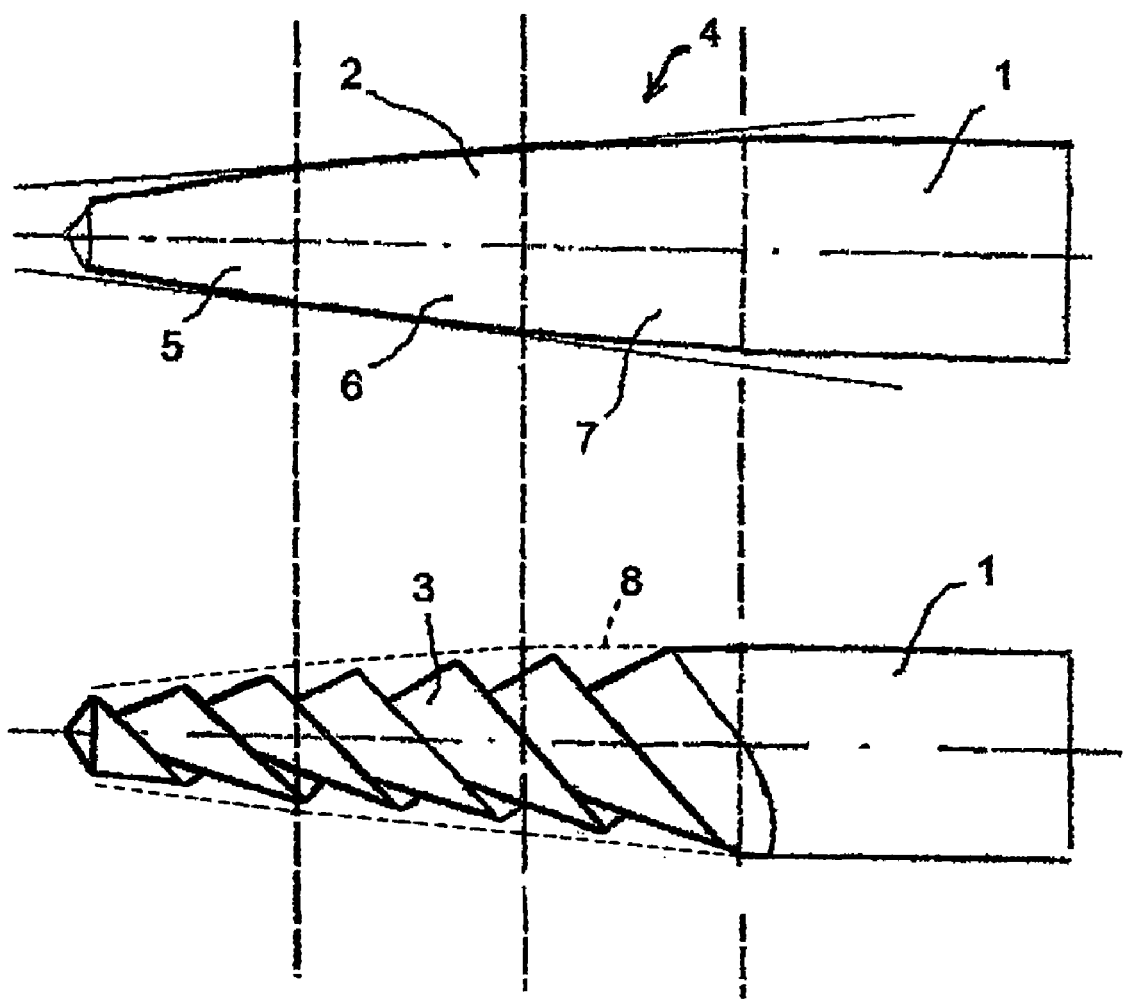
FIG. 3A is an elevational view of a conical blank having three different conicities, before machining.
FIG. 3B is an elevational view of the conical blank shown in FIG. 3A, after machining.

Apparatus capable of cutting cylindrical blanks to form instruments, and more particularly, to form blades that can be used in the field of endodontics, are known. For example, the above-mentioned U.S. Pat. No. 5,527,205, U.S. Pat. No. 5,628,674 and U.S. Pat. No. 5,655,950 describe an apparatus having a fixing device for holding the cylindrical blanks, and means for displacing the blanks in rotation and in translation in front of a grinder to form helical grooves in the blanks, and a blade that can be used for dental care.

In accordance with the present invention, a conical blank is cut with a machine which includes the following main components. A device is provided for loading the blanks in a hopper, and for bringing blanks which are to be machined to a working zone. A spindle is provided for receiving a blank, and for holding the blank during machining. A machining grinder is provided for cutting the blank which is driven in a movement perpendicular to the axis of the spindle. A guide is provided substantially opposite to the grinder, which operates to hold the blank during its machining, and which is displaced symmetrically relative to the grinder in relation to the axis of the spindle. A motorized drive is provided for rotating the blank about its axis, and for displacing the blank in a direction of advancement during the cutting procedure. Finally, a device is provided for unloading the machined piece.

In particular, the machining grinder has an axis of rotation which is parallel to the axis of the spindle, or which is included in a vertical plane parallel to the axis of the spindle. The axis of the grinder forms an angle with respect to a horizontal axis that varies as a function of the shape of the instrument which is to be obtained after cutting.

In accordance with the present invention, and referring to FIG. 1, a blank for producing an endodontic instrument has a cylindrical portion 1 and a generally conical portion 2. The cylindrical portion 1 is fixed in the spindle of the machining apparatus, and is held along part of its length during machining. The generally conical portion 2 is machined during displacement of the blank in front of the grinder, and has an overall shape which approximates, and which is slightly larger than the geometric envelope of the final shape which is to be given to the active part of the endodontic instrument after machining.

FIG. 2 shows the final instrument which is obtained after cutting the blank which is shown in FIG. 1. The active part 3 of the instrument, which is the portion of the instrument designed for preparation of the tooth canal by the practitioner, has several cutting edges.

The blank shown in FIG. 1 has a regular, generally conical portion 2. The conicity of the generally conical portion is preferably between 2 and 20%. The generally conical portion 2 of the blank does not exceed the final diameter of the instrument by more than 20%. In this way, the material to be removed during machining is reduced to the maximum extent.

Referring to FIGS. 1A and 1B, relative to FIGS. 2A and 2B, the material which is removed by machining of the blank is illustrated with reference to cross-sectional views taken at A-A and B-B in FIGS. 1 and 2. The illustrated cross-section of the final instrument (FIGS. 2A and 2B) shows, in this example, three cutting edges, which are obtained following three grinding operations for cutting three helical grooves.

The blank is preferably made from an alloy of titanium and nickel, although there is nothing which would exclude the use of steel, or different alloys. The present invention is all the more advantageous when the alloy used to produce the endodontic instrument is strong and difficult to machine since, compared to known techniques using cylindrical blanks, the amount of material to be removed is significantly reduced.

As shown in FIG. 2, the final endodontic instrument includes several helical cutting edges. The method of producing such an instrument, in accordance with the present invention, includes the following operations. A blank is provided which, in accordance with the present invention, has a generally conical portion which is to be machined, and a cylindrical portion which permits the blank to be fixed in the supporting spindle. The blank is then displaced in a direction of advancement, and is slowly driven in rotation in front of the rotary grinder, to cut a hollowed-out, helical groove which develops a first helical cutting edge. This process is repeated for a number of times corresponding to the number of cutting edges of the instrument.

The method for producing an endodontic instrument, in accordance with the present invention, employs a blank having a generally conical portion which approximates, and which is slightly larger than the envelope of the final shape to be given to the active part of the endodontic instrument after machining, including the cutting edges of the instrument. The generally conical portion preferably has a conicity between 2 and 20%, and the diameter of each section of the generally conical portion does not exceeding the final diameter of the instrument by more than 20%. The method of the present invention advantageously uses a blank produced from an alloy of nickel and titanium to produce the endodontic instrument.

The method of the present invention characteristically employs a speed of advancement of the blank of at least 200 mm per minute. The speed of advancement can be greater than 300 mm per minute for the production of an endodontic instrument from a blank having a conicity of 2%. Such speeds are to be compared with the much lower speeds of 5 inches per minute, i.e., 127 mm per min, which are indicated in the above-mentioned U.S. Pat. No. 5,527,205, U.S. Pat. No. 5,628,674 and U.S. Pat. No. 5,655,950.

The speed of advancement, combined with the speed of rotation of the blank about its axis, determines the pitch of the helix which is cut in the blank. This pitch can be constant or variable depending on the type of instrument to be produced. The machining tool used allows the various essential speeds to be controlled, namely, the speed of advancement of the blank, the speed of rotation of the blank along its axis, and the speed of rotation of the grinder.

The grinder can be inclined to produce different groove forms in the blank. The characteristics of the usable grinders can vary depending on the material of the blank and the type of instrument to be produced. For example, it is possible to use diamond grinders, vitrified grinders, etc.

By varying the adjustable parameters of the apparatus, a wide variety of endodontic instruments can be produced, and this can be done at very high speeds when compared to known techniques. The process of the present invention makes it possible to remove material in a summary fashion which is relatively fast, and which can even be an approximation of the final shape which is to be developed, if desired, with any fine machining then being performed on a separate apparatus.

In accordance with the present invention, instruments of different shapes can be produced. For example, and referring to FIG. 3A, it is possible to cut a blank 4 which has three different conicities 5, 6 and 7 extending along the generally conical portion 2. FIG. 3B shows the endodontic instrument which is obtained after machining, as previously described. In this illustration, the envelope 8 of the initial blank has been shown, surrounding the active part 3, in order to show that the material removed by grinding is very limited in volume, which in turn permits a very rapid machining speed.

Figures 4A, 4B:
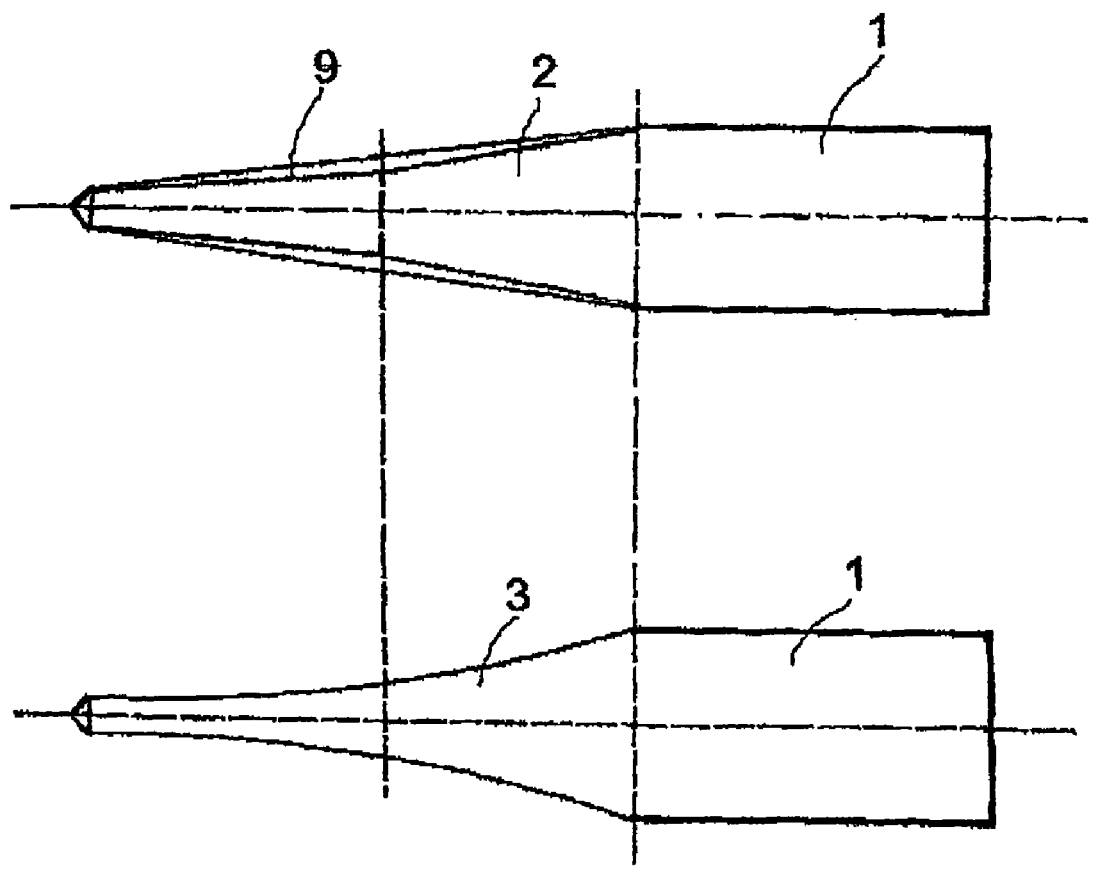
FIG. 4A is an elevational view of a conical blank having a variable conicity, for producing an instrument with a concave active part, before machining.
FIG. 4B is an elevational view of the conical blank shown in FIG. 4A, after machining.

FIG. 4A illustrates another alternative embodiment blank which can be used in accordance with the present invention. The blank of FIG. 4A can be used to produce an instrument which is tapered, and optionally smooth, having, for example, an active part 3 with a concave shape, as is shown in FIG. 4B. For producing this type of instrument, the generally conical portion of the blank represented in FIG. 4A can have a regular conicity or a variable conicity with a concave portion 9 close to that of the final instrument.

Numerous other blanks can be employed, in addition to the above-described, alternative embodiments. The length of the cylindrical portion, and of the generally conical portion, can vary relative to one another without departing from the scope of the present invention. Diverse shapes can also be designed, and the method of the present invention permits an extensive range of endodontic instruments to be obtained.

The method of the present invention can also be used with various apparatus having means for holding the blank, for placing the blank in the spindle, and for removing the machined part from the apparatus after it has been machined, once again, without departing from the scope of the present invention. The same applies to the motors and to the peripheral equipment which is used to allow the machining tool to operate optimally.

The grinder which is used to permit abrasion of the blank, to produce the helical grooves in the blank, can turn at different speeds. As an example, a speed of about 5500 revolutions per minute can be used for this. The grinder can further employ different abrasives, provided the resulting cutting is effective and ensures the highest possible speed of advancement of the blank.

The speed of advancement of the blank is generally the factor which limits the speed of production of the instrument. The speed of rotation of the blank about its axis can also vary within quite a wide range, depending on the instrument which is desired, on the efficacy of the grinding procedure, and on the speed of advancement of the blank. The several parameters governing the production of the instrument will logically vary depending on the material which is used to produce the blank.

After the desired instrument has been obtained, various unloading devices can be used to discharge the instrument which has been produced. The unloading device which is used can, if desired, be connected to a finishing and packaging line in order to permit maximum automation in serial production.

It will be understood that the present invention is not limited to the embodiments which have been described and illustrated, by way of example, and will instead further encompasses all technical equivalents and their combinations.

The invention claimed is:

1. A method for producing an endodontic instrument having at least one helical cutting edge, comprising the steps of:
   providing a blank having a cylindrical portion for fixing the blank in a supporting spindle, and a generally conical portion which is to be machined by a grinding process to form an active part of the endodontic instrument which includes the helical cutting edge, wherein the helical cutting edge of the active part of the endodontic instrument has a final shape which defines a first envelope, and wherein the conical portion of the blank has a shape which defines a second envelope which approximates, and which is slightly larger than the first envelope defined by the final shape of the helical cutting edge of the active part of the endodontic instrument after being machined;
   cutting a hollowed-out, helical groove which develops the helical cutting edge by displacing the blank in a direction of advancement, and slowly rotating the blank in front of a rotary grinder;
   repeating the cutting step for a plurality of times corresponding to a selected number of cutting edges for the endodontic instrument; and
   providing the conical portion of the blank with a diameter which does not exceed a corresponding diameter of the active part of the endodontic instrument by more than 20% for every diameter defined along the active part of the endodontic instrument.

2. The method of claim 1 which further includes the step of providing the conical portion with a conicity of between 2 and 20%.

3. The method of claim 1 wherein the active part has a plurality of sections, each having a diameter, and which further includes the step of providing the conical portion with a plurality of sections, each having a diameter which does not exceed the diameter of corresponding sections of the active part by more than 20%.

4. The method of claim 1 which further includes the step of forming the blank from an alloy of nickel and titanium.

5. The method of claim 1 which further includes the step of advancing the blank which is displaced in the direction of advancement at a speed of at least 200 mm per minute.

6. The method of claim 1 wherein the first envelope is a conical envelope.

7. A method for producing an endodontic instrument having at least one helical cutting edge, comprising the steps of:
   providing a blank having a cylindrical portion for fixing the blank in a supporting spindle, and a generally conical portion which is to be machined by a grinding process to form an active part of the endodontic instrument, wherein the conical portion of the blank has a shape which defines a first envelope;
   cutting a hollowed-out, helical groove in the conical portion of the blank while displacing the blank in a direction of advancement and slowly rotating the blank in front of a rotary grinder, developing a helical cutting edge in the active part of the endodontic instrument;
   repeating the cutting step for a plurality of times corresponding to a selected number of helical cutting edges for the endodontic instrument, forming the helical cutting edges of the active part in a final shape which defines a second envelope which approximates and which is slightly smaller than the first envelope after being machined; and providing the active part of the endodontic instrument with a diameter which is not reduced from a corresponding diameter of the conical portion of the blank by more than 20% for every diameter defined along the active part of the endodontic instrument.

8. The method of claim 7 which further includes the step of machining the cutting edges while cutting the helical groove in the conical portion of the blank so that the helical cutting edges have a final shape which is defined by the second envelope.

9. The method of claim 7 which further includes the step of providing the conical portion with a conicity of between 2 and 20%.

10. The method of claim 7 wherein the conical portion has a plurality of sections, each having a diameter, and which further includes the step of providing the active part with a plurality of sections, each having a diameter which is not reduced from the diameter of corresponding sections of the conical portion by more than 20%.

11. The method of claim 7 which further includes the step of forming the blank from an alloy of nickel and titanium.

12. The method of claim 7 which further includes the step of advancing the blank which is displaced in the direction of advancement at a speed of at least 200 mm per minute.

13. The method of claim 7 wherein the second envelope is a conical envelope.

14. A method for producing an endodontic instrument having at least one helical cutting edge, comprising the steps of:

providing a blank having a cylindrical portion for fixing the blank in a supporting spindle, and a generally conical portion which is to be machined by a grinding process to form an active part of the endodontic instrument, wherein the conical portion of the blank has a shape which defines a first envelope;

cutting a hollowed-out, helical groove in the conical portion of the blank while displacing the blank in a direction of advancement and slowly rotating the blank in front of a rotary grinder, developing a helical cutting edge in the active part of the endodontic instrument; and repeating the cutting step for a plurality of times corresponding to a selected number of helical cutting edges for the endodontic instrument, forming the helical cutting edges of the active part in a final shape which defines a second envelope which approximates and which is slightly smaller than the first envelope after being machined;

wherein the first envelope has a first circumference, wherein a circumscribed circle intersecting the helical cutting edges of the second envelope has a second circumference corresponding to the first circumference, and wherein the first circumference does not exceed the second circumference by more than 20% for every circumference defined along the active part of the endodontic instrument.

15. The method of claim 14 which further includes the step of machining the cutting edges while cutting the helical groove in the conical portion of the blank so that the helical cutting edges have a final shape which is defined by the second envelope.

16. The method of claim 14 which further includes the step of providing the conical portion with a conicity of between 2 and 20%.

17. The method of claim 14 wherein the conical portion has a plurality of sections, each having a circumference, and which further includes the step of providing the active part with a plurality of sections, each having a circumference which is not reduced from the circumference of corresponding sections of the conical portion by more than 20%.

18. The method of claim 14 which further includes the step of forming the blank from an alloy of nickel and titanium.

19. The method of claim 14 which further includes the step of advancing the blank which is displaced in the direction of advancement at a speed of at least 200 mm per minute.

20. The method of claim 14 wherein the second envelope is a conical envelope.

* * * * *